United States Patent

Vignola et al.

[11] Patent Number: 6,156,939
[45] Date of Patent: Dec. 5, 2000

[54] PROCESS FOR THE HYDROXYLATION OF AROMATIC HYDROCARBONS

[75] Inventors: Rodolfo Vignola, Monterotondo; Ezio Battistel, Cameriano; Daniele Bianchi, Arese; Rossella Bortolo; Roberto Tassinari, both of Novara, all of Italy

[73] Assignee: Enichem S.p.A., Milan, Italy

[21] Appl. No.: 09/542,457

[22] Filed: Apr. 4, 2000

Related U.S. Application Data

[62] Division of application No. 09/021,816, Feb. 11, 1998, Pat. No. 6,071,848.

[30] Foreign Application Priority Data

Feb. 27, 1997 [IT] Italy ................................ MI97A0434

[51] Int. Cl.$^7$ ...................................................... C07C 37/00
[52] U.S. Cl. ............................ 568/803; 568/629; 568/774
[58] Field of Search ..................................... 568/803, 629, 568/774

[56] References Cited

U.S. PATENT DOCUMENTS

| | | | |
|---|---|---|---|
| 3,692,842 | 9/1972 | Massie | 568/803 |
| 4,786,714 | 11/1988 | Drent . | |
| 4,859,646 | 8/1989 | Drent . | |
| 5,028,576 | 7/1991 | Drent et al. . | |
| 5,124,300 | 6/1992 | Drent . | |
| 5,149,880 | 9/1992 | Sawyer | 568/803 |

OTHER PUBLICATIONS

Seizo Tamagaki et al., "Hydroxylation of Benzene by Hydrogen Peroxide Catalyzed by an FE$^{3+}$—Catechol Catalyst Supported on Silica Gel", Chemistry Letters, The Chemical Society of Japan, No. 5, pp. 651–652, May 1982.

Kazuhiko Hotta et al., "Hydroxylation of Benzene with Hydrogen Peroxide by the Use of Hydrophobic Catechols and FE$^{3+}$Complexes as the Catalyst", Chemistry Letters, The Chemical Society of Japan, No. 6, pp. 789–790, Jun. 1981.

Derwent Abstracts, Accession No. 96–207693, Prodn. of Pyrocatechol and Hydroquinone—Comprises Reacting Phenol with AQ. Hydrogen Peroxide in Presence of Bivalent Iron Sulphate as Catalyst, RU2043331, Sep. 10, 1995.

Derwent Abstracts, Accession No. 95–281983, Prepn. of Prod. of Pyrocatechol and Hydroquinone for Use as Dye Intermediate—Includes Reacting Phenol @ with AQ. Hydrogen Peroxide with Di:Valent Iron Sulphate as Catalyst, RU2028287, Feb. 9, 1995.

*Primary Examiner*—Michael L. Shippen
*Attorney, Agent, or Firm*—Oblon, Spivak, McClelland, Maier & Neustadt, P.C.

[57] ABSTRACT

The invention relates to a process for the hydroxylation of aromatic hydrocarbons by direct oxidation with hydrogen peroxide. The process is carried out in the presence of a catalyst comprising:
iron, administered as inorganic salt;
iron ligand, consisting of carboxylic acids of ether-aromatic compounds containing nitrogen, in particular pyrazin-2-carboxylic acid and derivatives;
acidifying agent, especially trifluoracetic acid, and a solvent system comprising an organic phase consisting of a substrate and acetonitrile and an aqueous phase containing the catalyst and hydrogen peroxide.

7 Claims, No Drawings

PROCESS FOR THE HYDROXYLATION OF AROMATIC HYDROCARBONS

This application is a divisional application of U.S. Ser. No. 09/021,816, filed Feb. 11, 1998, now U.S. Pat. No. 6,071,848.

The invention relates to a process for the hydroxylation of aromatic hydrocarbons by direct oxidation of hydrogen peroxide.

More specifically, it relates to a process for the preparation of phenols in which the oxidation of the substrate with hydrogen peroxide is carried out in the presence of a particular catalytic system containing iron, an iron ligand and an acidifying agent and a biphasic solvent system.

The invention also relates to the catalyst used for the oxidation.

The production of phenol based on the hydroxylation of benzene has been studied since the 70s'.

The considerable number of publications on the matter is indicative of the efforts made in research in this field. In particular, research has been based on the use of transition metals and relative complexes as catalysts in the oxidation of hydrocarbons. (Ed. D. H. R. Barton et al., Plenum, New York, 1993; G. B. Shul'pin et al., J. Chem. Soc. Perkin Trans, 1995, 1459).

Although illustrating the catalytic capacities of these compounds, the articles show how the low conversion of the substrate, the presence of undesired by-products and the low selectivity of the oxidating agent make industrial embodiment of direct oxidation reaction unsatisfactory.

The critical points indicated mainly concern the oxidating agent, the catalyst (metal-ligand complex) and the solvent system.

Hydrogen hydroperoxide is considered as being one of the most promising among oxidating reagents owing to its low cost and its capacity of producing only water as by-product.

It is, in fact, widely used in oxidation reactions of alkanes, alkyl-aromatic compounds and arenes carried out in the presence of catalysts consisting of complexes of transition metals. (R. A. Sheldon et al., "Metal-Catalyzed Oxidations of Organic Compounds" Academic Press, New York, 1981; G. B. Shul'pin et al., J. Cat. 1993, 142, 147).

The solvent system is the basis of the control not only of the yields but also the ratios between the products obtained.

The catalyst regulates the reaction rate.

Its activity is influenced by the metal and posssible ligand of which it is composed.

Among the reaction systems which have been developed for the oxidation of hydrocarbons, the Fenton and Gif systems are the most widely studied. The Fenton system, consisting of $Fe^{11}/H_2O_2$ in water at pH 2, is based on the production of the hydroxyl radical which seems to be the active oxidative species (J. Stubble et al., Chem. Rev., 1987, 87, 1107).

The reaction is exploited to oxidate aromatic hydrocarbons; in the case of benzene the hydroxyl radical directly attacks the aromatic ring with the consequent formation of phenol.

This reaction is accompanied by other collateral reactions with a consequent decrease in the selectivity with respect to the phenol.

The formation of undesired products, such as biphenyl or polyhydroxylated compounds which tend to polymerize (via formation of quinones), form a definite limit of this system for the production of phenol, for the purposes of industrial development.

The Gif system like the Fenton system comprises the use of a catalyst based on iron and $H_2O_2$ as oxidating agent. The characteristic element of this system is the mixture of pyridine and acetic acid used as solvent. It is generally used for the conversion of saturated hydrocarbons in ketones (H. R. Barton et al., J. Am. Chem. Soc. 1992, 114, 2147; C. Sheu et al., J. Am. Chem. Soc. 1990, 112, 1936).

The role of pyridine as blocking agent of the hydroxylic radicals which are formed in the reaction medium, is considered fundamental for overcoming the limits relating to the Fenton system. In general, with the different substrates used, such as cyclohexane and adamantane, the use of iron in the form of simple salts is less effective than in the form of complex salts. In these complexes the iron is in the presence of ligands of the picolinic acid type which is by far the most widely used.

In spite of the various studies carried out, the effective nature of the catalyst in solution and the actual role of the ligand is still not clear (D. H. R. Barton et al., Tetrahedron Lett. 1996, 37,1133).

The importance of the solvent system is evident from the investigations of Sheu et al. in which substitution with acetonitrile of the pyridine/acetic acid system determines a reduction in the efficiency and selectivity (C. Sheu et al., J. Am. Chem. Soc. 1990, 112, 1936). In this context subsequent data in literature show that acetonitrile can be an effective solvent provided the presence of pyridine is ensured in adequate quantities (D. H. R. Barton et al., Tetrahedron Lett. 1996, 37, 8329).

Experiments carried out by Menage et al. show that benzene is not oxidated in this system (S. Menage et al., J. Mol. Cat. 1996, 113, 61).

A process has now been found for the preparation of phenols by the direct oxidation of an aromatic substrate which enables much higher selectivity values of hydrogen peroxide and conversions of the substrate and productivity to be obtained with respect to the processes described of the known art.

In particular the present invention relates to a process for the preparation of phenols having the formula:

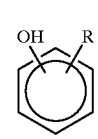

(I)

wherein R is a group selected from hydrogen, a $C_1$–$C_8$ linear or branched alkyl, a $C_1$–$C_8$ alkoxy, a halogen, a carbonate, nitro, by the direct oxidation with hydrogen peroxide of an aromatic compound having the formula:

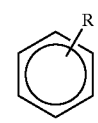

(II)

wherein R has the meaning previously defined, characterized in that the oxidation reaction is carried out in the presence of a catalytic system as defined in the previous claims and a solvent system consisting of an organic phase made up of the aromatic compound and acetonitrile and an aqueous phase containing the catalytic system and hydrogen peroxide.

The invention also relates to the catalyst used for the oxidation.

The double phase of which the solvent consists, extracts the phenol from the aqueous phase, where the reaction takes place, reducing the possibility of subsequent oxidations.

The reaction system used determines a high conversion of the aromatic hydrocarbon, of up to 15%, and a high selectivity with respect to the hydrogen peroxide, of up to 90%.

These values are much higher than those quoted in literature.

In the reaction system of the present invention, the phenols are produced by the direct oxidation in liquid phase of the aromatic hydrocarbon with hydrogen peroxide in the presence of a catalyst based on iron.

The catalyst can be administered both as $Fe^{+2}$ and as $Fe^{+3}$ in the form of chloride, sulfate, nitrate or perchlorate, preferably as sulfate and more preferably as $FeSO_4 * 7H_2O$.

Iron ligands which can be used are carboxylic acids of heteroaromatic compounds containing nitrogen, such as picolinic acid, dipicolinic acid, isoquinolin-1-carboxylic acid, pyrazin-2-carboxylic acid, 5-methyl-pyrazin-2-carboxylic acid N oxide, preferably pyrazin-2-carboxylic acid and its N oxide.

The acidifying agent can be either an inorganic acid, such as sulfuric acid or an organic acid, such as p-toluene-sulfonic acid, methane-sulfonic acid, pyrazin-2-carboxylic acid and trifluoracetic acid, preferably trifluoracetic acid.

The liquid phase consists of a double phase in which the organic phase is made up of the aromatic hydrocarbon and an organic solvent, the aqueous phase contains the catalyst and hydrogen peroxide.

Acetonitrile has proved to be the most effective organic solvent; for the purposes of the yield and selectivity it is considered a determinant component for the particular reaction system.

The volume ratio in the organic phase between the aromatic substrate and organic solvent can be between 1 and 6, preferably close to 5.

The organic phase and the aqueous phase can be distributed according to different volumetric ratios; it is preferable to have a ratio of the phases close to 1 in the reaction mixture.

The reagents, aromatic hydrocarbon and hydrogen peroxide can be present in the reaction mixture according to a molar ratio of between 10 and 3; it is preferable to have a ratio approximate to 10.

For the formation of the catalyst the molar ratio between the iron and ligand can be between 2 and 5, preferably 4; the molar ratio between the acid and iron can vary from between 6 and 2, and is preferably approximate to 2.

For the activation of the hydrogen peroxide the molar ratio between $H_2O_2$ and the iron can be between 20 and 100, preferably 50.

The reaction temperature can be between 40 and 80 degrees centigrade, preferably 70.

The reaction time, under the best conditions, can be between 3 and 15 minutes.

The recovery of the phenol and the possibility of recycling the catalyst are particularly facilitated in this reaction system.

The normal physico-chemical techniques can be used for recovering the phenol from the organic phase in which it is present in about 90%. Due to the removal of the product, it is possible to recycle the catalyst situated in the aqueous phase.

The following examples provide a further illustration of the present invention without limiting its scope.

EXAMPLE 1

0.03 mmoles of iron as $FeSO_4*7H_2O$ (5.56 mg) and 0.1 mmoles of pyrazin-2-carboxylic acid were charged into a 50 ml flask.

6.45 ml of water and 0.07 mmoles of trifluoracetic acid (2.45 ml of an aqueous solution 0.32% by weight) were subsequently added.

18.6 mmoles of benzene (1.66 ml) and 9.16 ml of acetonitrile were then added.

The reaction was activated with the addition of 1.86 mmoles of hydrogen peroxide (0.22 ml of an aqueous solution at 30%).

The reaction was carried out at 70 degrees centigrade for 10 minutes under magnetic stirring and reflux cooled.

At the end of the reaction the products and reagents were analyzed.

The results were:

Conversion of $H_2O_2$ (percentage of initial mmoles used up in the reaction): 78%

Selectivity of $H_2O_2$ (percentage of mmoles used up, converted into phenol): 75%

Conversion of benzene (percentage of initial mmoles transformed): 6%

Selectivity of phenol (percentage of mmoles of benzene converted into phenol): 95%

EXAMPLE 2

The procedure of example 1 was repeated except that the ligand used was 5-methyl-pyrazin-2-carboxylic acid N oxide (0.1 mmole).

The results obtained were:

Conversion of $H_2O_2$: 93%

Selectivity of $H_2O_2$: 86%

Conversion of benzene: 8%

Selectivity of phenol: 96%

EXAMPLE 3

The procedure of example 1 was repeated except that 0.02 mmoles of iron as $FeSo_4*7H_2O$ were introduced. The results were:

Conversion of $H_2O_2$: 63%

Selectivity of $H_2O_2$: 70%

Conversion of benzene: 4.5%

Selectivity of phenol: 95%

EXAMPLE 4

The procedure of example 3 was repeated except that different quantities of trifluoracetic acid were used.

The results obtained are shown in table 1.

TABLE 1

| TFA (mmoles) | Conv. $H_2O_2$ (%) | Sel. $H_2O_2$ (%) | Conv. Benz. (%) | Sel. Phenol (%) |
|---|---|---|---|---|
| 0.20 | 74 | 44 | 3.3 | 94 |
| 0.10 | 68 | 48 | 3.4 | 94 |
| 0.07 | 63 | 70 | 4.5 | 96 |
| 0.05 | 68 | 54 | 3.8 | 95 |
| 0.02 | 60 | 49 | 3.0 | 95 |

EXAMPLE 5

The procedure of example 3 was repeated except that different Ligand/iron (L/Fe) rations were tested. The results obtained are shown in table 2.

TABLE 2

| L/Fe | Conv. $H_2O_2$ (%) | Sel. $H_2O_2$ (%) | Conv. Benz. (%) | Sel. Phenol (%) |
|---|---|---|---|---|
| 2 | 84 | 40 | 3.4 | 95 |
| 3 | 84 | 76 | 6.0 | 96 |
| 5 | 63 | 70 | 4.5 | 96 |

EXAMPLE 6

The procedure of example 1 was repeated except that different quantities of $H_2O_2$ were introduced into the reaction mixture.
The results obtained are shown in table 3.

TABLE 3

| $H_2O_2$ (mmoles) | Conv. $H_2O_2$ (%) | Sel. $H_2O_2$ (%) | Conv. Benz. (%) | Sel. Phenol (%) |
|---|---|---|---|---|
| 1.86 | 78 | 76 | 6 | 96 |
| 3.72 | 99 | 71 | 14 | 95 |
| 7.44 | 93 | 44 | 16 | 94 |

EXAMPLE 7

The procedure of example 1 was repeated except that different types of acidifying agents were experimented at different concentrations.
The results obtained are shown in table 4.

EXAMPLE 8

The procedure of example 1 was repeated except that benzene was replaced by toluene.
The results obtained were:
Conversion of $H_2O_2$: 83%
Selectivity of $H_2O_2$: 60%
Conversion of toluene: 3%
Selectivity of cresol: 70%

TABLE 4

| Acids | Conc. mM | Conv. $H_2O_2$ (%) | Sel. $H_2O_2$ (%) | Conv. Benz. (%) | Sel. Phen. (%) |
|---|---|---|---|---|---|
| TFA | 3.5 | 96 | 76 | 3.4 | 95 |
| pTSA | 3.5 | 96 | 58 | 2.6 | 94 |
| $H_3PO_4$ | 0.2 | 83 | 54 | 2.0 | 94 |
| $HPF_6$ | 5.0 | 16 | 20 | 0.15 | 92 |
| MSA | 2.5 | 93 | 55 | 2.4 | 94 |
| PRZCA | 7.5 | 94 | 61 | 2.7 | 96 |

TFA = trifluoracetic
pTSA = p-toluenesulfonic
$HPF_6$ = hexafluorophosphoric
MSA = methansulfonic
PRZCA = pyrazin-2-carboxylic

We claim:

1. A process for the preparation of phenols having the formula:

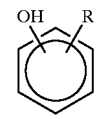

(I)

wherein R is a group selected from hydrogen, a $C_1$–$C_8$ linear or branched alkyl, a $C_1$–$C_8$ alkoxy, a halogen, a carbonate, nitro, by the direct oxidation with hydrogen peroxide of an aromatic compound having the formula:

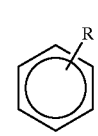

(II)

wherein R has the meaning previously defined, characterized in that the oxidation reaction is carried out in the presence of a catalytic system comprising iron in the form of an inorganic salt, carboxylic acids of aromatic compounds containing nitrogen and trifluoracetic acid and solvent system consisting of an organic phase made up of the aromatic compound and acetonitrile and an aqueous phase containing the catalytic system and hydrogen peroxide.

2. The process according to claim 1 characterized in that in the solvent system the volume ratio between aromatic compound and acetonitrile is about 5.

3. The process according to claim 1 characterized in that the ratio between the organic phase and the aqueous phase is about 1.

4. The process according to claim 1 characterized in that the ratio between the aromatic compound and the hydrogen peroxide is about 10.

5. The process according to claim 1 characterized in that the molar ratio between the hydrogen peroxide and the iron of the catalytic system is about 50.

6. The process according to claim 1 characterized in that the reaction is carried out at about 70° C. and for a time of 10 minutes.

7. The process according to claim 1 characterized in that R, in the compounds having formula (I) and (II), is hydrogen.

* * * * *